US010398354B2

(12) United States Patent
Fuss et al.

(10) Patent No.: US 10,398,354 B2
(45) Date of Patent: Sep. 3, 2019

(54) SENSOR ARRAY SYSTEM (71) Applicant: ROYAL MELBOURNE INSTITUTE OF TECHNOLOGY, Melbourne, Victoria (AU)

(72) Inventors: Franz Konstantin Fuss, Reservoir (AU); Yehuda Weizman, East Melbourne (AU); Batdelger Doljin, Bundoora (AU)

(73) Assignee: Swinburne University of Technology, Hawthorn (AU)

( * ) Notice: Subject to any disclaimer, the term of this patent is extended or adjusted under 35 U.S.C. 154(b) by 444 days.

(21) Appl. No.: 14/903,663

(22) PCT Filed: Jul. 9, 2014

(86) PCT No.: PCT/AU2014/000703
§ 371 (c)(1),
(2) Date: Jan. 8, 2016

(87) PCT Pub. No.: WO2015/003211
PCT Pub. Date: Jan. 15, 2015

(65) Prior Publication Data
US 2016/0166178 A1 Jun. 16, 2016

(30) Foreign Application Priority Data
Jul. 12, 2013 (AU) ................. 2013902584

(51) Int. Cl.
A61B 5/103 (2006.01)
A61B 5/00 (2006.01)

(52) U.S. Cl.
CPC .......... A61B 5/1038 (2013.01); A61B 5/4064 (2013.01); A61B 5/7257 (2013.01);
(Continued)

(58) Field of Classification Search
CPC ... A61B 5/1038; A61B 5/4064; A61B 5/7257; A61B 5/7271; A61B 5/7405; A61B 5/742
(Continued)

(56) References Cited

U.S. PATENT DOCUMENTS 5,253,656 A 10/1993 Rincoe et al.
5,678,448 A 10/1997 Fullen et al.
(Continued)

FOREIGN PATENT DOCUMENTS

WO WO-2012/055029 A1 5/2012

OTHER PUBLICATIONS

Shu, L. et al., "In-Shoe Plantar Pressure Measurement and Analysis System Based on Fabric Pressure Sensing Array," IEEE Transactions on Information Technology in Biomedicine, vol. 14, No. 3, 2010.*

(Continued)

Primary Examiner — Daniel L Cerioni
(74) Attorney, Agent, or Firm — Harness, Dickey & Pierce, P.L.C.

(57) ABSTRACT

A system is provided for assessing heard injury criterion (HIC) by analyzing signals received from sensors of a sensor array to calculate an impact force on an impact area, determine the linear acceleration based on the impact force and mass of the wearer's head. HIC values are calculated within a variable duration sliding window across a time period within which an impact occurs based on the integral of linear acceleration for the time period of the window, to determine a maximal HIC which is converted to a biofeedback signal.

19 Claims, 10 Drawing Sheets (52) U.S. Cl.
CPC .......... *A61B 5/7271* (2013.01); *A61B 5/742* (2013.01); *A61B 5/7405* (2013.01); *A61B 5/486* (2013.01); *A61B 5/6803* (2013.01); *A61B 5/743* (2013.01); *A61B 5/7415* (2013.01); *A61B 5/7455* (2013.01); *A61B 2503/10* (2013.01); *A61B 2562/0247* (2013.01); *A61B 2562/0252* (2013.01); *A61B 2562/046* (2013.01)

(58) Field of Classification Search
USPC ........................................................ 600/592
See application file for complete search history.

(56) References Cited

U.S. PATENT DOCUMENTS

| | | | |
|---|---|---|---|
| 6,507,669 B1* | 1/2003 | Klassen | H04N 1/64 382/170 |
| 7,867,285 B2 | 1/2011 | Clausen et al. | |
| 8,002,672 B2 | 8/2011 | Brunner | |
| 8,122,772 B2 | 2/2012 | Clausen et al. | |
| 2005/0131317 A1* | 6/2005 | Oddsson | A61B 5/1038 600/592 |
| 2005/0184878 A1 | 8/2005 | Grold et al. | |
| 2007/0027369 A1* | 2/2007 | Pagnacco | A61B 5/1071 600/301 |
| 2008/0025640 A1* | 1/2008 | Trudeau | H04N 5/23248 382/294 |
| 2008/0064965 A1* | 3/2008 | Jay | A61B 5/02028 600/484 |
| 2010/0087900 A1* | 4/2010 | Flint | A61B 5/1101 607/104 |
| 2010/0204930 A1* | 8/2010 | Gustafsson | B23Q 1/385 702/41 |
| 2012/0109013 A1 | 5/2012 | Everett et al. | |
| 2014/0309752 A1* | 10/2014 | Yuzurihara | G05B 15/02 700/13 |
| 2016/0007902 A1* | 1/2016 | Hewson | A61B 5/11 600/592 |

OTHER PUBLICATIONS

International Search Report and Written Opinion of the ISA for PCT/AU2014/000703, ISA/AU, Woden ACT, dated Sep. 15, 2014.

* cited by examiner

SENSOR ARRAY SYSTEM

CROSS REFERENCE TO RELATED APPLICATIONS

This application is a 371 U.S. National Stage of International Application No. PCT/AU2014/000703, filed Jul. 9, 2014, and published in English on Jan. 15, 2015 as WO 2015/003211 A1. This application claims the benefit of and priority to Australian Patent Application No. 2013902584, filed Jul. 12, 2013. The disclosures of the above applications are incorporated herein by reference.

This invention relates to a sensor array that may provide biofeed back on the application of pressure in a number of situations particularly in footwear for gait analysis.

BACKGROUND TO THE INVENTION

Sensing of pressure on a surface has applications in footwear, beds and sports sensing for impacts.

In shoe sensors and gait analysis using sensors have been proposed particularly for to prosthetics.

U.S. Pat. No. 5,253,656 discloses a matrix array of pressure sensors particularly for bed sores and displays the signals to highlight the location of hotspots.

U.S. Pat. No. 5,678,448 discloses an in-shoe sensor array and audible signals prompted by a threshold pressure being exceeded.

U.S. Pat. No. 7,867,285 discloses a prosthetic shoe that incorporates bending sensors to sense the applied pressures and to control the heel and sole of the prosthetic shoe.

U.S. Pat. No. 8,002,672 discloses a treadmill with an array of pressure sensors and software that presents visual images of the pressure patterns. There is no disclosure of using auditory feedback and there are no detailed algorithms disclosed.

U.S. Pat. No. 8,122,772 discloses a shoe system for gait analysis and provides an algorithm for an activity index. The system provides audio signal feedback for the user to identify gait characteristics.

The development of instrumented insoles and shoes for pressure measurement is known. However the technological advancement and practical applicability depends on several parameters such as: accuracy of the sensors; resolution of the instrumented sole (sensor density namely the number of sensors on the insole per unit area); data sampling frequency; number of data channels; wireless data transfer rate; mathematical algorithms for improving low accuracy, density and data sampling rate; mathematical algorithms for calculating the centre of pressure (COP); mathematical algorithms for biofeedback signals; and, most importantly, the affordability and costs of smart insoles for therapeutic use (including the ratio of accuracy to costs).

It is an object of this invention to provide a sensor array and software that can provide a useful signal output and also bio feedback for users to modify their motion and improve posture and gait.

BRIEF DESCRIPTION OF THE INVENTION

To this end the present invention provides a system including a sensor array, a processor and a signal output device which calculates at least one advanced pressure parameter related to the array data and the processor analyses the inputs from the sensor array and provides over time a signal indicative of the magnitude of the advanced pressure parameter.

The advanced pressure parameter may be the location, speed and distribution of the centre of pressure (COP) and the fractal dimension of the COP. Other attributes such as location of hotspots and pressure impulses may be used.

Thus in a more preferred aspect the invention provides a system including a sensor array, a processor and a signal output device, in which the software installed in the processor calculates the location, speed and distribution of the centre of pressure on the array, analyses the inputs from the sensor array and provides over time, a signal to the signal output device which is indicative of the magnitude and movement of the centre of pressure.

A sensor grid is provided which is able to provide signals of the magnitude and location on the grid of applied pressure. In the prime application of gait analysis, the sensor in the sole of a shoe provides over time a signal indicative of the magnitude and movement of the centre of pressure. The minimum number of sensors in a defined area is 3. The movement of the centre of pressure may be presented as a visual signal showing the location of the centre of pressure on the outline of the sole with pressure values coded in colour. Alternatively the location may be represented as pitch of an audio signal and the magnitude by sound volume. Such a signal may be used to provide feedback to a patient to correct their gait by modifying their gait to produce a desirable signal. The analysis software uses an algorithm to identify the location, speed and distribution of the centre of pressure (COP) and additionally to assess the fractal dimension of the COP. Other attributes such as location of hotspots and pressure impulses may be used to augment the biofeedback signals.

The sensor system may be used in other sensing applications such as measuring impacts in sports or pressure points in patients confined to sitting or prone positions. In the prior art the sensor arrays and software were unsuitable for measuring locating and tracking COP.

The sensor array may be any conventional sensor type such as pressure sensitive material which has resistive, capacitive or piezoelectric properties. In this invention the sensor may be "sensorless" in that no conventional sensor is used. By providing a grid of wires or electrode strips on either side of the pressure sensitive material, or on one side of the pressure sensitive material only, a pressure sensitive grid is established. If the grid is located on one side of the pressure sensitive material only, insulating material is provided at the intersection of wires or strip electrodes running perpendicular to each other. This enables use of a larger area of material with wires across, vertically on one side, horizontally on the other, or vertically and horizontally on one side only, instead of cutting the system of this invention may be used in a range of applications.

Smart insoles for different purposes:
1): for training of small foot muscles, gait mapping (load distribution, rehab); as art tools (dancing, music); activity classification (exercising, military surveillance). The displays may be simple pressure distribution mapping or biofeedback as auditory and visual displaying the location and movement of centre of pressure so that participants can see their own output.
2) for medical applications such as diabetes, polyneuropathy, stroke and fall prevention. The displays may be advanced pressure distribution mapping or biofeedback as auditory and visual displaying location of centre of pressure and hotspot (concentrated pressure) mapping and pressure impulse of hotspots. The displays can assist in prevention of overloading hotspots (pressure ulcer prevention and therapy) and teaching load shift between 2 feet (golf swing assessment) or pressure distribution between 2 legs (running, detection of overlading of one leg. The indication of overload on one side may be with an acoustic biofeedback system on the same side; or fading out music on the same side).

3) for use in exoskeletons for para/quadriplegics and military use. These may provide biofeedback as auditory and/or visual signals to provide threshold control for activation of exoskeleton.

Smart sport shoes for use in football, soccer, kick training to provide biofeedback as auditory and/or visual signals to display location of centre of pressure and its pressure rate.

Prostheses/amputation stumps to provide auditory and/or visual signals to display location of hotspot (concentrated pressure) and its pressure impulse; pressure rate.

Wound management, including the treatment, prevention, rehabilitation of discontinuities and other injuries of the intact skin.

Seating (chairs, wheelchairs, automotive, aerospace, saddles) to display pressure distribution as an indicator of fatigue or health and safety concerns. The biofeedback as auditory and/or visual signals may display pressure rate, speed of centre of pressure.

Smart mats (intelligent mattresses, hospital beds, yoga mats) to display pressure distribution as an indicator of sleep profile and aid in baby monitoring and preventing pressure ulcers. The biofeedback as auditory and/or visual signals may display location of hotspot (concentrated pressure) and its pressure impulse; pressure rate.

Smart helmets for the recording of injury record, impacts and brain injury risk. The biofeedback as auditory signals may indicate magnitude of deceleration, jerk and the head injury criterion. The biofeedback as visual signals may display deceleration and jerk vectors and their origin with respect to a virtual head, as well as the head injury criterion as a vector or sphere with respect to a virtual head.

Smart gloves used in boxing and martial arts for scoring and measuring injury risk. The biofeedback as auditory and/or visual signals may display magnitude of both deceleration and jerk, as well as the head injury criterion.

Smart walkways for passenger or pedestrian monitoring over time and also vehicle monitoring to provide statistics. The biofeedback as auditory and/or visual signals may display centre of pressure (location of person), direction and speed (monitoring of traffic); children's playgrounds (music for amusement, safety monitoring); control of gates (pedestrians queuing up in front of a gate, measured by a smart walkway during rush hour would result in opening further gates by switching a red light signal to green in front of a door, as a biofeedback signal).

Insoles, force plates or posturographic plates (4 individual plates): for measurement of fall risk, instability, vertigo, etc.

Smart walls for target scoring.

Smart vests or garments with multiple sensors or layers of materials (sensorless sensing) for biofeedback of internal (muscle pressure) and external forces (drag forces, e.g. in skiing, cycling and swimming), indicating the pressure centre and the overall pressure as a biofeedback signal. Also they may be used to detect changes in muscle pressure and vibrations (compression garments) indicating the muscle activation pattern and the magnitude of muscle vibrations as a biofeedback signal.

Vibration monitoring: muscle vibrations when wearing compression garments; industrial applications for health and safety.

The surface array may also be used in gaming applications or in treadmills or wall climbing.

The position of the instantaneous COP may be determined by averaging the product of pressure magnitude and x- or y-coordinate of each sensor along the x- and y-axes of the Cartesian sensor matrix coordinate system, whereby the COP is expressed in terms of x- and y-coordinates of a Cartesian coordinate system or in terms of angle and radius of a polar coordinate system. The Cartesian or polar coordinates may be converted to biofeedback signals.

The velocity of the instantaneous COP may be determined from differentiating the displacement of the COP in x- and y-directions with time, and the velocity of the COP may be converted to biofeedback signals.

The distribution of the COP about its average point may be calculated from the standard deviation, root mean square, skew, or Kurtosis of the COP in x- and y-directions, or from the size of the area containing maximally 100% of the COP-locations within a defined time period. The distribution of the COP about its average point may be converted to biofeedback signals.

A fall index may be calculated from either the standard deviation, or root man square, skew, or Kurtosis of the COP in x- and y-directions, or from the size of the area containing maximally 100% of the COP-locations within a defined time period. The magnitude of the fall index may be converted to biofeedback signals.

A system as claimed in claim 8 wherein the fractal dimension of the movement of the COP in x- and/or y-direction is calculated from conventional methods for determining the fractal dimension of a signal, and where the magnitude of the fractal dimension is converted to biofeedback signals.

The pressure rate of at least one sensor point may be determined from differentiating the pressure with time; and where the pressure rate may be converted to biofeedback signals.

The force may be calculated by integrating the pressure over the effective sensor area, and the linear acceleration (perpendicular to the area of the sensor array) may be calculated by dividing the force by the effective mass of the object, body, or parts of the body, which the sensor array is attached to, or in contact with, and the user-induced acceleration is calculated from the linear acceleration by subtracting the gravitational acceleration. The magnitude of force and/or acceleration may be converted to biofeedback signals.

When used in assessing head injury criterion, the head Injury criterion may be calculated from the highest value obtained from multiplying the integral of acceleration over time by the inverse of the time period, raising this product to the power of 2.5, and multiplying the result by the time period; the time period ranges between 1 millisecond and 15 milliseconds and the integral is calculated within this variable time period window continuously across the acceleration signal. Preferably only the maximal HIC value is taken, obtained from combining different time periods and initial times. The magnitude of the Head Injury Criterion may be converted to biofeedback signals.

The impulse of pressure or force may be calculated from integrating the pressure or force with time, and the magnitude of the impulse may be converted to biofeedback signals.

Developing high pressure areas (hotspots) may be identified from the pressure or force impulse of at least one sensor node. The magnitude of the impulse and/or the distance between the hotspot and the physiological path of the COP may be converted to biofeedback signals.

The pressure or force magnitude may be subjected to thresholds and the pressure data may be converted into a histogram of at least two bins, and the data in each bin may be used for a scoring system to count the number of repetitive movements based on different pressure or force levels. A positive or negative score may be converted to biofeedback signals.

Vibrations may be identified with fast Fourier transform of the signal. Mean, median or impulse of the power spectrum may be converted to biofeedback signals.

The linear velocity of the body centre of mass may be calculated from integrating the linear acceleration with time; where the displacement of the body centre of mass is calculated from integrating the linear velocity with time. Work and energy may be calculated from integrating the force with displacement. Power may be calculated from the product of force and velocity. The magnitude of velocity, displacement, work or power may then be converted to biofeedback signals.

The magnitude of the advanced pressure parameter may converted to an auditory, visual or tactile biofeedback signal. The auditory biofeedback signal may be pitch- and/or volume-, and/or melody-coded. The visual biofeedback signal may be colour- and/or brightness-coded, and/or a flashing light signal, and/or a display on a screen. The tactile biofeedback signal may involve vibrations, pressure, or electrical stimulation.

DETAILED DESCRIPTION OF THE INVENTION

Preferred embodiments of the invention will now be described with reference to the drawings in which.

Figure 1:
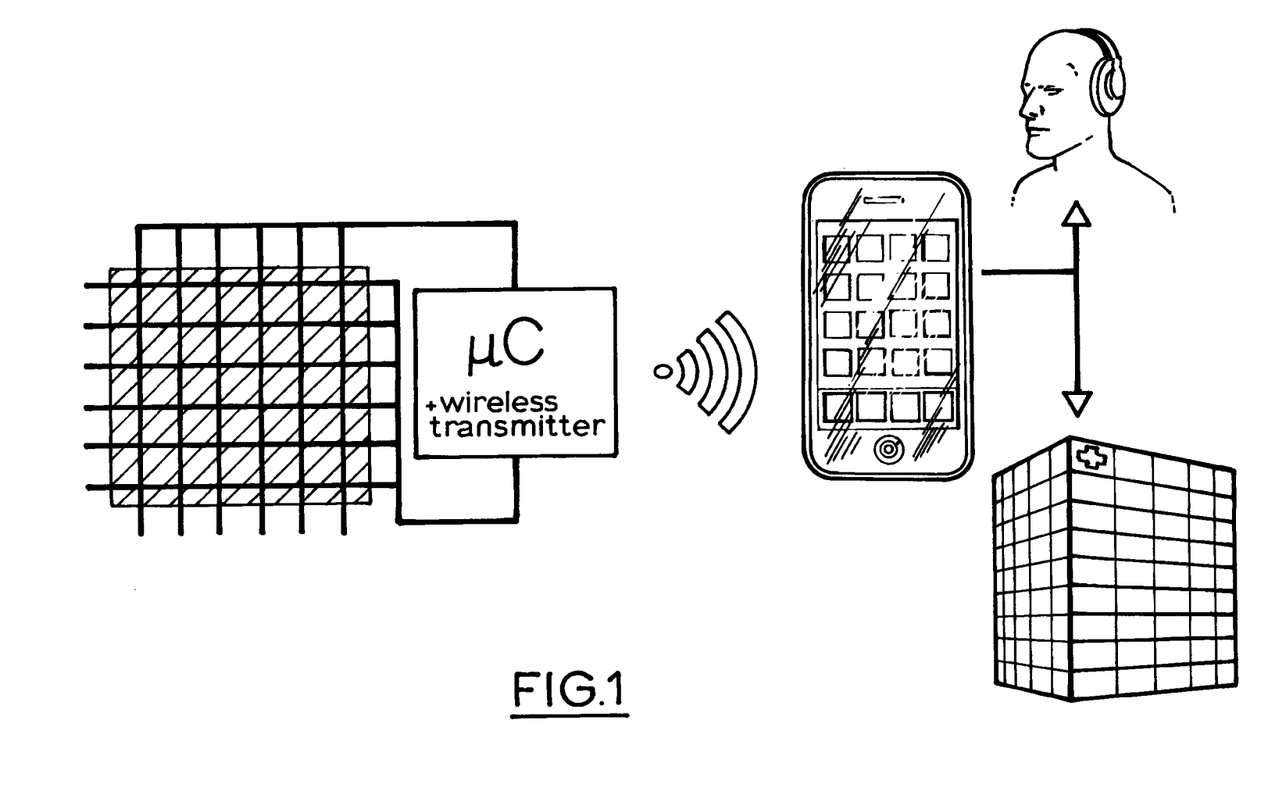
FIG. 1 illustrates the principle of this invention.

The principle of the invention is shown in FIG. 1.
The device consists of:
sensorless pressure mapping via microcontroller
signals/data sent to smart phones
signals/data sent to earphones for biofeedback
signals/data sent to hospital (data record, D2H2; distributed diagnosis and home health care)
algorithms for converting raw pressure data to advance pressure parameters, and subsequently to biofeedback signals (pitch- and volume-coded auditory signal; 2D or 3D colour- and brightness coded visual signal in terms of an image or graph)
advanced pressure signals are: location and speed of centre of pressure, magnitude of pressure rate; pressure impulse; hotspot location.

The pressure data are measured by sensors or materials, which have resistive, capacitive or piezoelectric properties, and react to different types of internal and/or surface pressures, such as compressive stress, tensile stress, bending stress, torsional stress, or shear stress.

Figure 2:
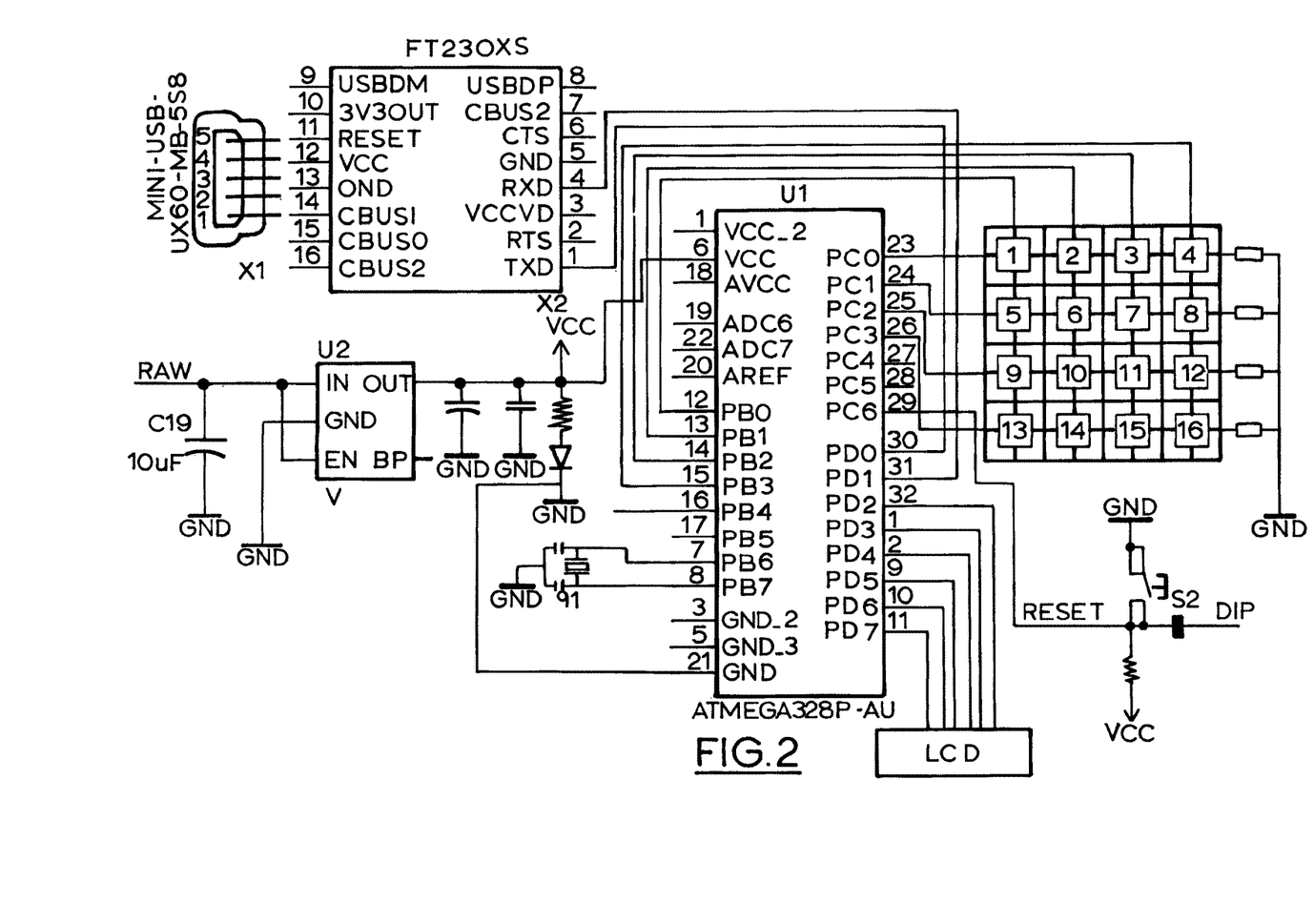
FIG. 2 depicts the general device layout of one embodiment of the invention.
Figure 3:
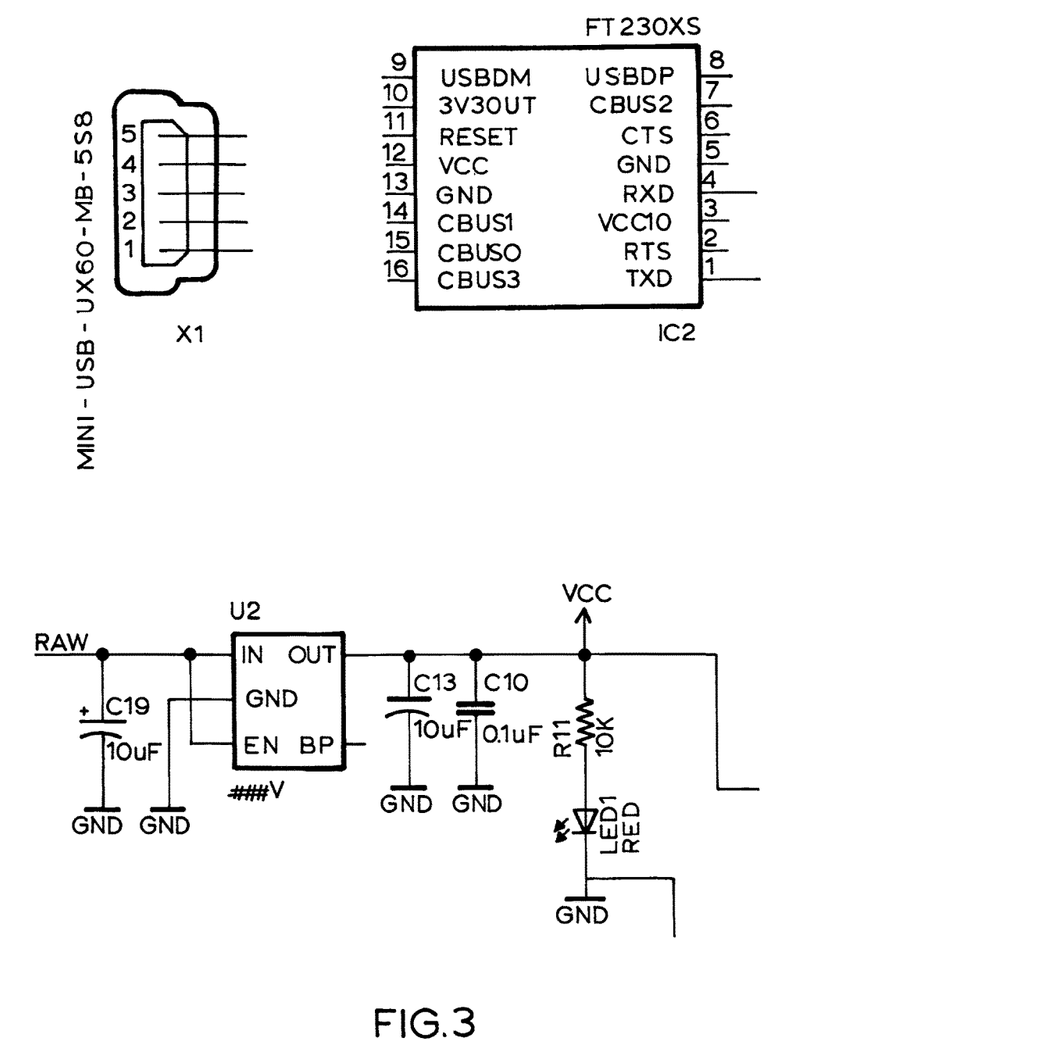
FIG. 3 illustrates in more detail components x1, IC2 and U2 shown in FIG. 2.
Figure 4:
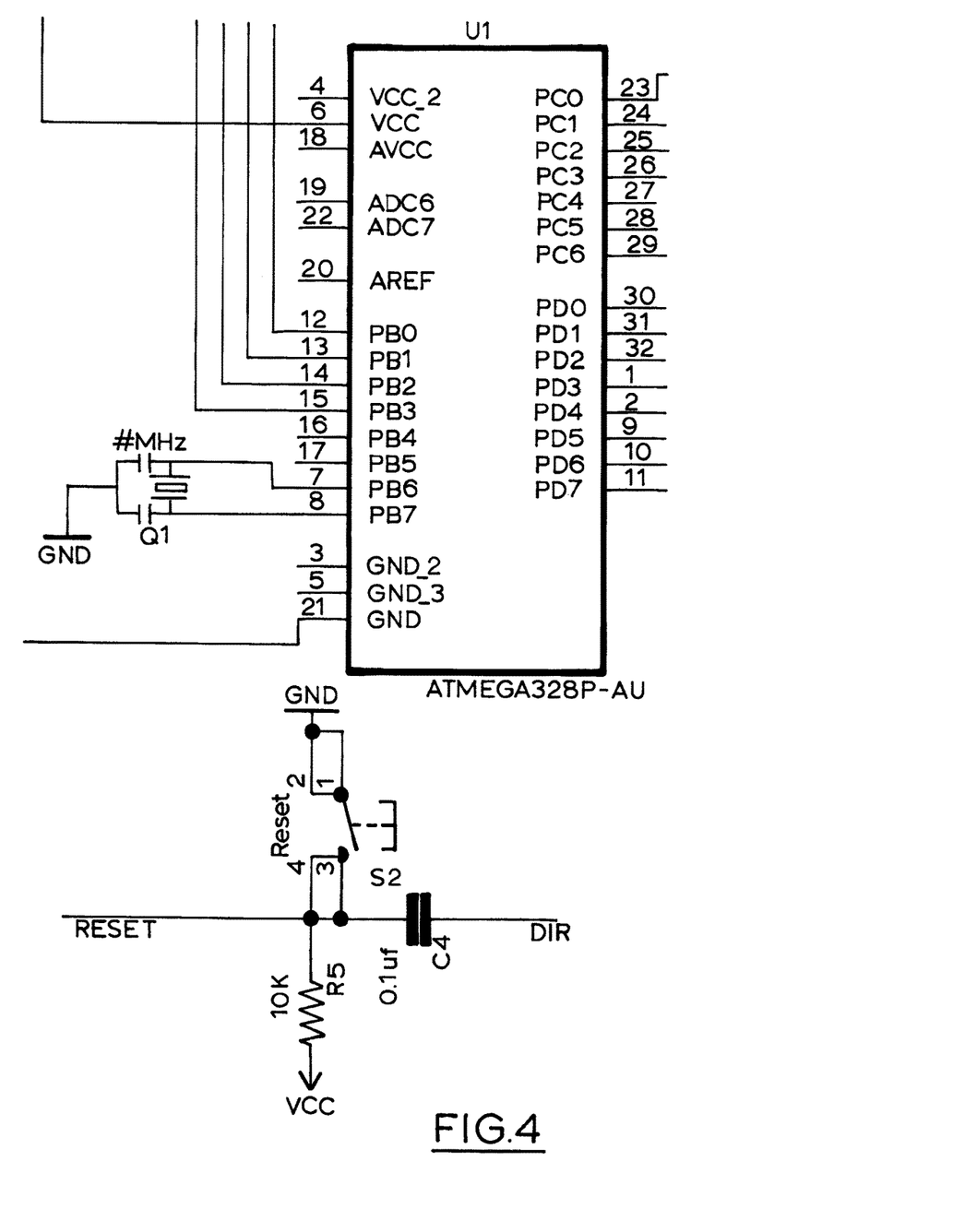
FIG. 4 illustrates in more detail components U1 and reset shown in FIG. 2.

The schematic outline of a preferred system for measuring the pressure of a resistive sensor matrix is shown in FIG. 2:

The U1 (Programmable micro-controller chip) is connected to the grid, 4×4/16 cells/Sensors.

These connections are as follows:
4× Digital (0v/5v) outputs, pins—12,13,14,15, connected vertically from left to right.
4× Analog inputs, pins—23, 24, 25, 26, connected horizontally from top to bottom, to read data from reference resistors (equivalent to cells change in value).
the code controls:
the digital ports (0 v/5 v)—vertical cells (1,5,9,13), (2,6, 10,14), . . .
and analogue reading ports—horizontal cells (1,2,3,4), (5,6,7,8,), . . .

The micro controller is programmed such that the multiplexer runs as follows:
1. Digital output (pin 12) generates 5v, all other digital outputs generate 0v. Analogue port (reading the voltage) runs from top to bottom and reads the voltage from 4 reference resistors (essentially read cells 1, 5, 9, 13).
2. Digital output (pin 13) generates 5v, all other digital outputs generate 0v. Analogue port (reading the voltage) runs from top to bottom and read the voltage from 4 reference resistors (essentially read cells 2, 6 10, 14)
3. Digital output (pin 14) generates 5v, all other digital outputs generate 0v. Analogue port (reading the voltage) runs from top to bottom and reads the voltage from 4 reference resistors (essentially reads cells 3,7,11,15).
4. Digital output (pin 15) generates 5v, all other digital outputs generate 0v. Analogue port (reading the voltage) runs from top to bottom and reads the voltage from 4 reference resistors (essentially reads cells 4, 8, 12,16)

This covers 16 readings from 16 cells (4×4).

The 4×4 matrix (16 sensors) can be expanded to any matrix.

The overall output is a single channel file with repeated raw data sets from sensors 1-16 consecutively (1-16, 1-16, 1-16, etc), recorded at a specific data sampling frequency.

The number of reference resistors required corresponds to the number of analogue ports.

Figure 5:
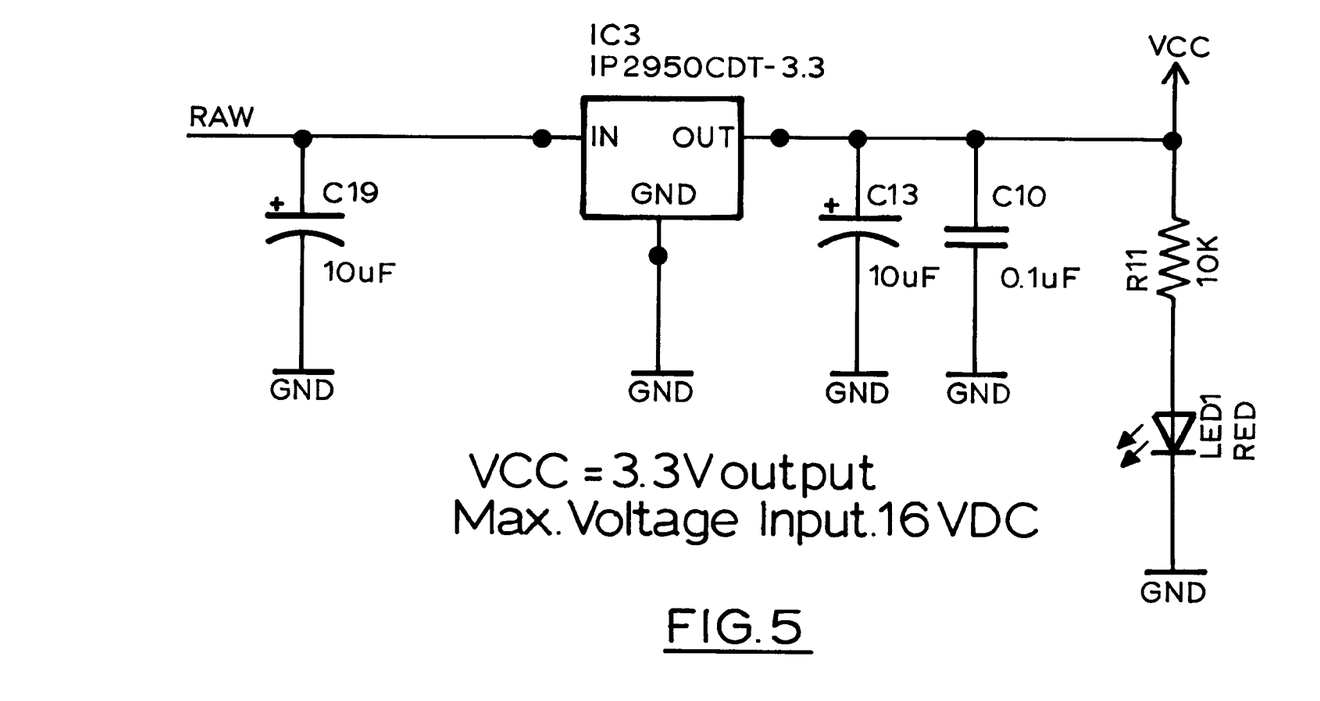
FIG. 5 illustrates a step down DC/DC converter to supply stable conditioned power.

FIG. 5 depicts step down DC/DC converter IC3 regulates input (battery) voltage down to 3.3V. C19 C13 C10 caps filter out any high and low band noise and provide stable conditioned power source to the rest of the circuit.

Figure 6:
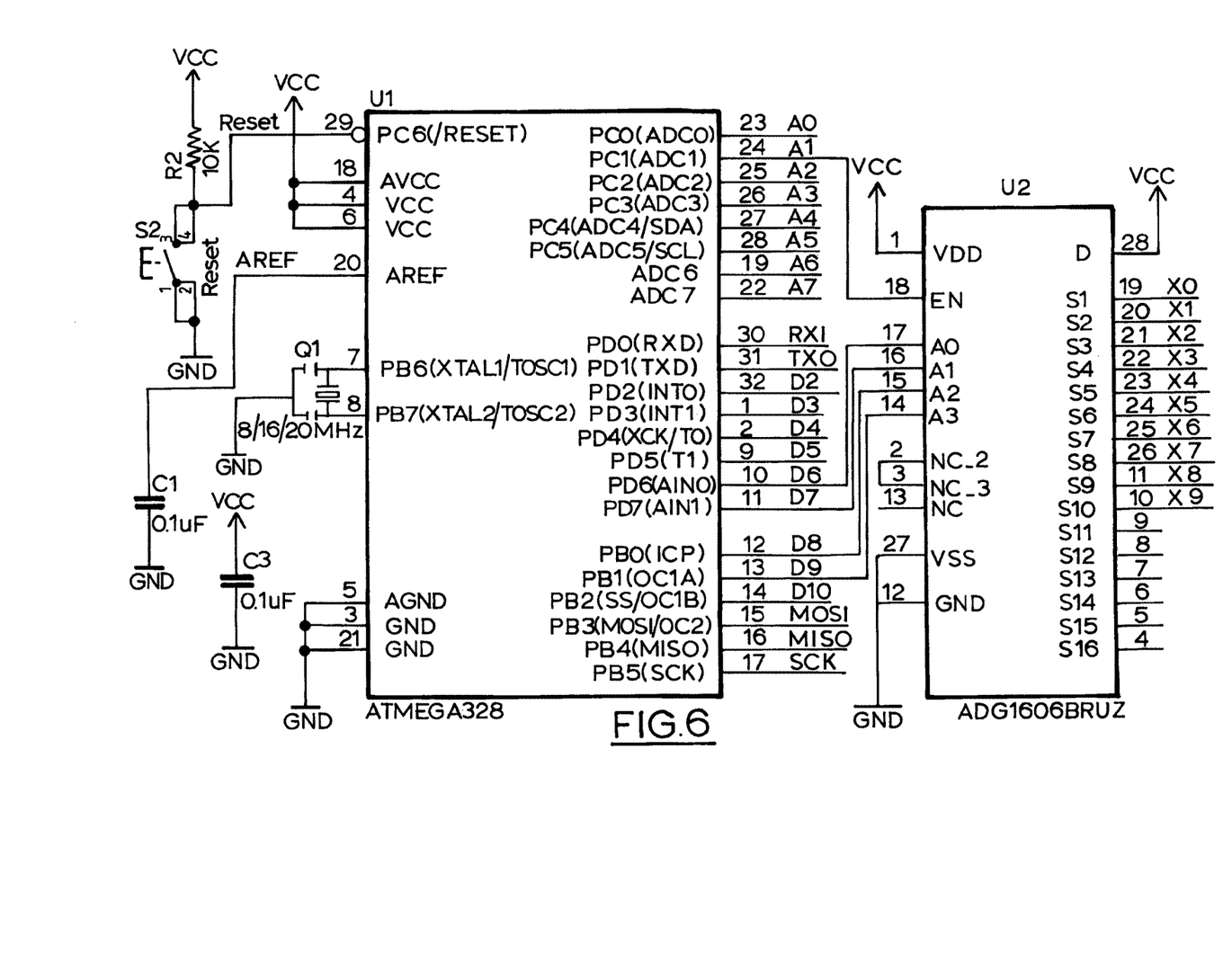
FIG. 6 depicts a microcontroller for processing data from the sensors.

FIG. 6 depicts an 8 bit AVR micro controller U1 processes all the data collected from sensor; multiplexer U2 controls 2×2 (4 sensor cells) matrix sensor circuit, which runs on 4 bit binary address which can control up to 16×16 (256) matrix sensor and R1 is reference resistor for the sensor.

Figure 7:
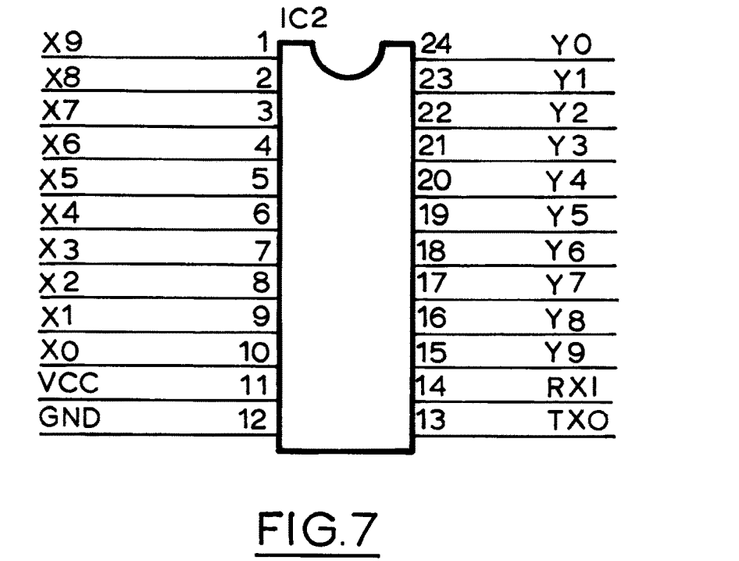
FIG. 7 depicts a multiplexing circuit.

FIG. 7 depicts sensor connector IC2 connects the main board to the insole sensor.

Figure 8:
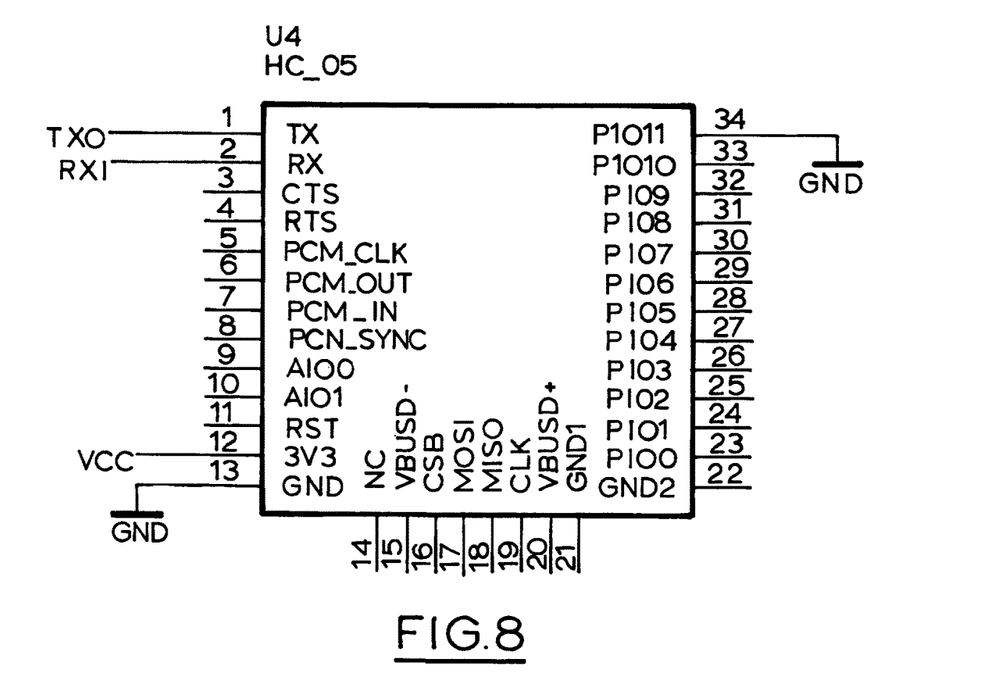
FIG. 8 depicts a blue tooth module for communication to external devices.

FIG. 8 depicts a bluetooth module U4 which communicates with external devices over wireless technology.

Figure 9:
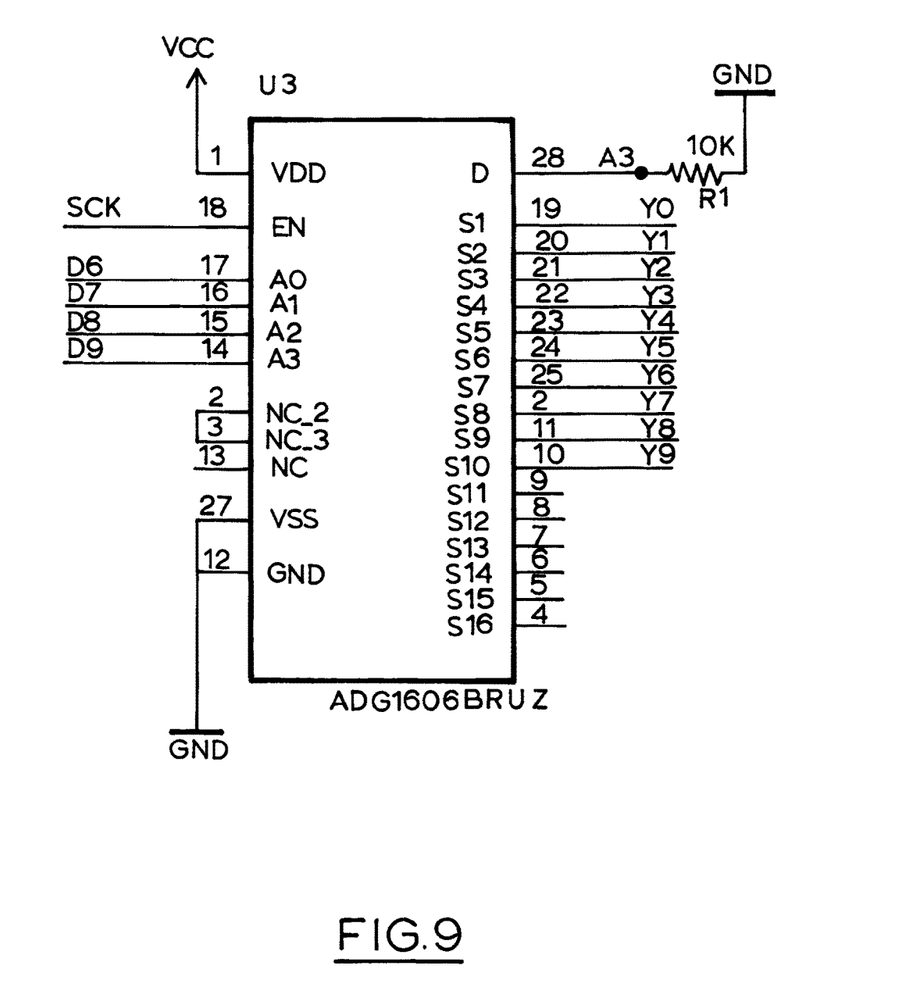
FIG. 9 depicts a sensor circuit.

FIG. 9 depicts multiplexers U2 and U3 control 2×2 (4 sensor cells) matrix sensor circuit, which runs on 4 bit binary address which can control up to 16×16 (256) matrix sensor and R1 is reference resistor for the sensor.

Figure 10:
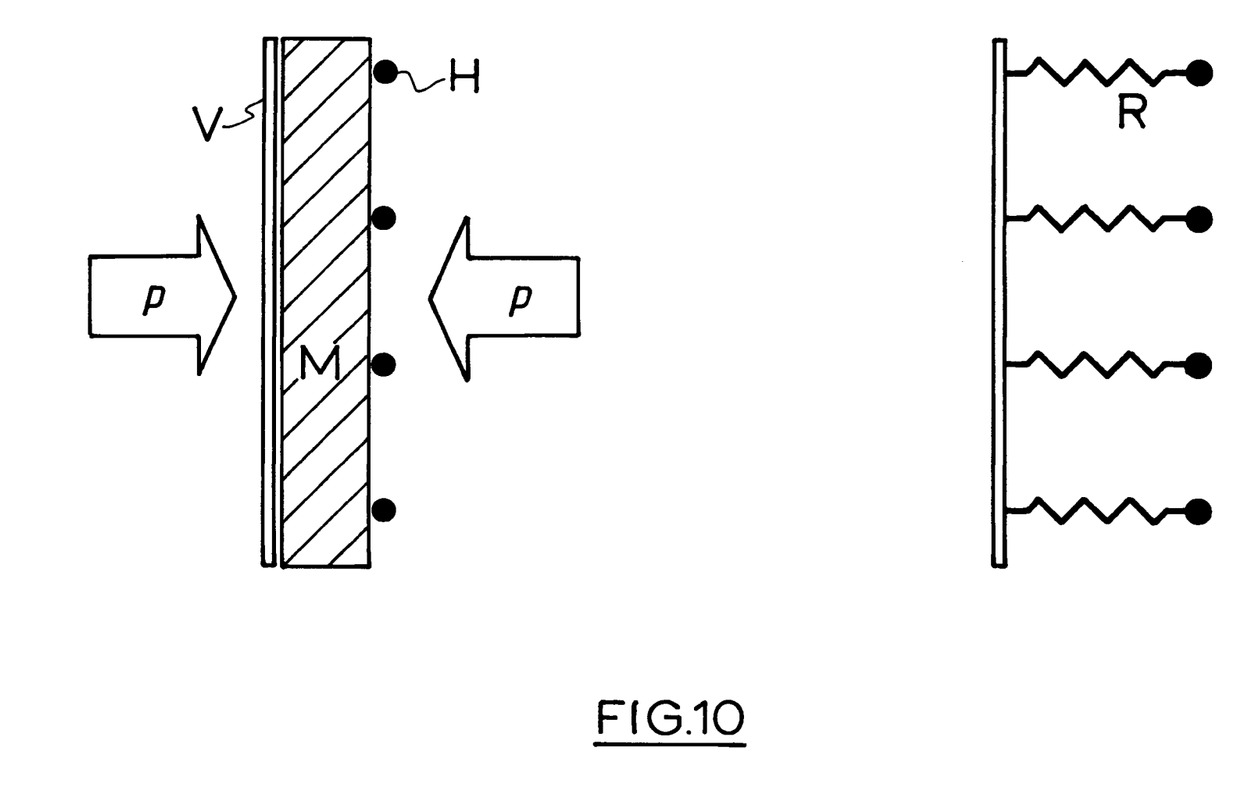
FIG. 10 shows the cross section of a double sided sensor grid (schematic and circuit equivalent)
Figure 11:
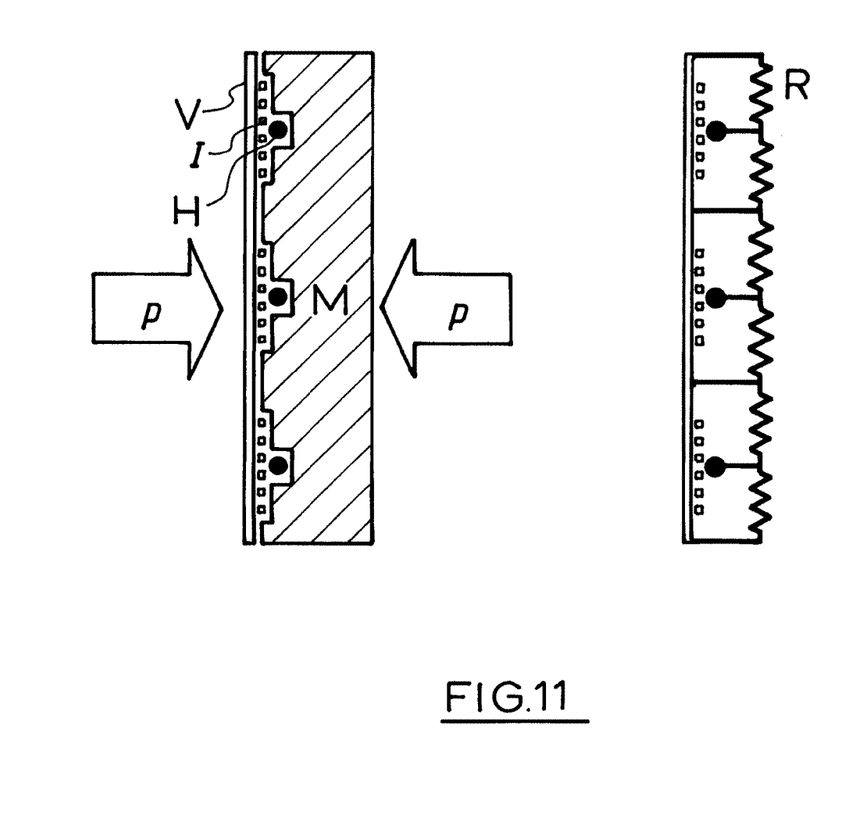
FIG. 11 shows the cross section of a single sided sensor grid (schematic and circuit equivalent).

FIGS. 10 and 11 illustrate the cross section of a sensor grid (schematic and circuit equivalent); double sided in FIG. 10 and single sided in FIG. 11 where:
V=vertical electrode,
H=horizontal electrode,
M=conductive material,
I=insulating layer,
R=resistor,
p=pressure The data is sent to output (earphones, smartphone, computer, screen) either tethered or wirelessly, for real time biofeedback (auditory, visual) or post-measurement biofeedback (visual).

The sensor materials for sensorless measurement may be any resistive, capacitive or piezoelectric sensor.
1) Conductive solid polymers/elastomers (e.g. vinyl, velostat or neoprene).
2) Antistatic cellular materials (e.g. PE foam, containing pre-compounded carbon black)
3) Conductive fabrics The advanced pressure parameters are calculated from the pressure measured by the sensors. The word sensor below has to be replaced by "electrodes", when applying sensorless sensing. Basically, at least two sensors are required for determining advanced pressure parameters; in sensorless sensing, at least 3 electrodes are required for a one-dimensional array measuring two pressure areas of interest; and at least 4 electrodes are required for a two-dimensional array measuring four pressure areas of interest.

Basically, an acoustic biofeedback signal can be volume or pitch coded.

E.g. for converting the magnitude of the pressure to a biofeedback signal, the larger the pressure, the louder is the tone; or the higher is the pitch of the tone.

In a dual parameter signal, one parameter can be volume-coded, and the other pitch-coded.

These two parameters can be:
position of the COP in x- and y-direction
position of the COP in x- and y-direction
distance of the COP from a centre point (pitch-coded), and magnitude of the average pressure (volume-coded; bullseye approach)
angle of the COP-vector (pitch-coded), and magnitude of the average pressure (volume-coded; circular/elliptic keyboard approach)
angle of the COP-vector (pitch-coded), and distance of the COP from a centre point (volume-coded; circular/elliptic keyboard approach)

In a triple parameter signal, one parameter can be volume-coded, and the other two pitch-coded by a sound consisting of 2 harmonic tones.

As an example, the magnitude of the pressure will be volume coded and the angle of the COP-vector pitch-coded. When walking with an instrumented insole, the task is to achieve a melody signal which is unique for each COP path, and changes if the COP path is altered.

The task of the user is to achieve a consistent replication of the specific melody pattern at every stride.

The advanced pressure parameters to be calculated from the raw pressure data, and to be converted to biofeedback signals (as per the invention described), are:

a) Location of the (Instantaneous) Centre of Pressure (COP):

If pressure is distributed (unevenly) over a surface, then the COP is defined as the intersection of at least two lines about which the moments generated by forces (per unit area, distributed over an area) on either side of each line are balanced. The accurate determination of the instantaneous COP requires evenly distributed sensors over the measurement area with a high resolution.

$$COPx = \sum_{i=1}^{n} \frac{x_i p_i}{n}$$

$$COPy = \sum_{i=1}^{n} \frac{y_i p_i}{n}$$

where COPx and COPy are the coordinates of the COP; $x_i$ and $y_i$ are the distances of the $i^{th}$ sensor from the origin of the sensor matrix coordinate system; $p_i$ is the pressure on the $i^{th}$ sensor, and n is the total number of sensors.

Alternatively, $$\theta = ATAN2 \frac{COPy}{COPx}$$

$$R = \sqrt{COPx^2 + COPy^2}$$

where theta $\theta$ is the polar angle of the COP, A TAN 2 is the "$2^{nd}$" inverse tangent function (returning the polar angle in any of the 4 quadrants), and R is the distance between the COP and the origin of the coordinate system.

Application: biofeedback of the current location of the COP, e.g. on the foot sole in running, sitting, etc.; load shift between 2 legs; golf swing assessment with biofeedback; location of the COP on the head when wearing a helmet for locating the point of impact; location of the moving COP on front and back side of rowing oar blades or paddle blades Auditory biofeedback: the biofeedback signal can be generated by
converting the polar angle theta $\theta$ to a pitch coded sound and/or the distance R to a volume coded sound, or vice versa;
converting the COPx coordinate to a pitch coded sound and/or the COPy coordinate to a volume coded sound, or vice versa;
converting the distance between the actual COP location and the ideal COP location to a volume or pitch coded sound.

b) Speed of the COP:

The instantaneous COP moves over an area, and the first time derivative of the displacement of the COP equals its speed.

$$v_{COP} = \sqrt{v_x^2 + v_y^2}$$

where $v_{COP}$ is the resultant speed of the COP, and $v_x$ and $v_y$ are the speed components defined by $$v_{x,y} = \frac{x_{t+1}, y_{t+1} - x_t, y_t}{\Delta t}$$

where x and y are the coordinates of the COP, and $\Delta t$ is the data sampling frequency.

Application: biofeedback of running speed or posturographic instability; load shift between 2 legs; golf swing assessment and biofeedback.

Auditory biofeedback: the biofeedback signal refers to the magnitude of the COP speed, and is either volume or pitch coded.

c) Distribution of the COP About its Average Point:

Due to instability, vibrations or external force, the COP can rapidly move within a defined area about its average point (ideal or expected point). The parameters of the COP movement are the distance between the average point and the current instantaneous COP, as well as the speed of movement, which is directly related to the aforementioned distance.

Application: biofeedback of posturographic instability, estimation of the fall risk The distribution of the COP is calculated from:
the standard deviation of the COP about the ideal point or across a coordinate axis,
root-mean-square RMS of the COP about the ideal point or across a coordinate axis,
skewness of the COP about the ideal point or across a coordinate axis,
Kurtosis of the COP about the ideal point or across a coordinate axis,
average velocity of the COP about the ideal point or across a coordinate axis,
size of the area covered by 100% or less than 100% (e.g. 95%, 90% . . . ) by the movement of the COP.

Auditory biofeedback: the magnitude of the standard deviation, of the RMS, of the skewness, of the Kurtosis, of the average velocity, and/or of the area is converted to a volume or pitch coded sound. The advanced COP parameters can be combined to a fall index, converted to a volume or pitch coded sound, alerting the user (e.g. via a smart insole) of the risk of falling.

d) Fractal Dimension of the COP Movement

The fractal dimension of a signal reflects its degree of chaos. The more rapid the changes of the COP in e.g. anterior-posterior or medio-lateral direction, the higher is its fractal dimension. The fractal dimension of a signal, preferably its Hausdorff dimension, can be calculated with conventional methods (Higuchi method, Sevcik method, box counting methods, etc.).

$$D_H = \frac{\log N}{\log r} + C$$

where $D_H$ is the Hausdorff dimension, r is the radius or diameter of a box, N is the number of boxes at a specific r, and C is a constant.

Application: biofeedback of posturographic instability, estimation of the fall risk Auditory biofeedback: the magnitude of the fractal dimension is converted to a volume or pitch coded sound.

e) Magnitude of the Pressure Rate

Whereas the magnitude of the pressure signal can be directly converted to a biofeedback signal, the instantaneous rate of the pressure signal has to be calculated from the time derivative of the pressure signal. The pressure rate equals the force rate per unit area; and the force rate equals the jerk times the mass (jerk=$4^{th}$ time derivative of the displacement).

$$\dot{p} = \frac{p_{i+1} - p_i}{\Delta t}$$

where $\dot{p}$ is the pressure rate

Application: biofeedback of the pressure rate or force rate; the pressure rate or force rate is related to the severity of tissue injuries, and the biofeedback serves for injury monitoring.

Auditory biofeedback: the magnitude of the pressure rate is converted to a volume or pitch coded sound f) Head Injury Criterion The Head Injury Criterion HIC serves for assessing the severity of brain injury sustained after an impact of a specific acceleration a or force F. Force and acceleration are related to each other through $$F = m\,a$$

where m is the effective mass of the head.

The HIC is calculated from $$HIC = \max\left[\Delta t\left(\frac{1}{\Delta t}\int_{t_1}^{t_2} a\, dt\right)^{2.5}\right]$$

where a is the linear acceleration, $t_1$ and $t_2$ denote the beginning and end of the acceleration spike, and $\Delta t = t_2 - t_1$; $\Delta t$ is maximally 15 milliseconds.

HIC>1000 is considered dangerous.

Application: biofeedback of the HIC in head impacts, when wearing a smart helmet, smart head protection gear, or a smart boxing glove, whereby the biofeedback serves for head impact monitoring, scoring system in boxing and martial arts, as well as for learning of how to avoid dangerous head impacts by behavioural changes.

Auditory biofeedback: the magnitude of the HIC is converted to a volume or pitch coded sound; or the auditory signal is fed back only if a threshold is exceeded.

g) Location of Hotspots

Hotspots are determined by constantly updating the maximal pressure per sensor so that the current pressure map reflects the maximal pressure of each sensor measured so far.

Application: biofeedback of the location of high pressure areas, as well as biofeedback on how to avoid overloading hotspots.

Auditory biofeedback: the magnitude of the distance between the COP and a hotspot is converted to a volume or pitch coded sound, whereby the biofeedback serves for hotspot monitoring, as well as for learning of how to avoid overloading a hotspot by increasing the distance between the hotspot and the path of the COP.

h) Determination of the Pressure Impulse

The pressure of each sensor is integrated with time and the current pressure impulse is reflected on the pressure map.

$$S_p = \int_{t_0}^{t} p\, dt$$

where $S_p$ is the pressure impulse.

Application: biofeedback of the location of areas with high pressure over time.

Auditory biofeedback: the magnitude of the pressure impulse is converted to a volume or pitch coded sound i) Determination of the Correct COP Location in Combination with the Correct Force or Pressure Range This combined, advanced pressure parameter serves as a scoring system, e.g. for martial arts, where boxing gloves and body vests are equipped with sensors or sensorless sensing systems, or for counting repetitive movements when exercising on a pressure-sensitive mat. Specific and defined areas of the vests must be hit for scoring a point (COP within these areas). Other areas are out of bounds (COP within these areas) and hitting them results in deduction of one point. At the same time, the pressure is measured by both the gloves and the vests, and if the pressure is within the specified range, (combined with the COP in the right area) leads to scoring a point. If the pressure is too low, then no point is scored. If the pressure is too high, then a point will be deducted if the COP is in the right area, or 2 points if the COP is in the wrong area. Equipping both vests and gloves serves to identify accidental own hits, or if one's own glove is sandwiched between one's own vest and the opponents glove. In these cases, the opponent does not score a point.

j) Determination of Vibrations

The time series of a pressure signal is subjected to FFT (Fast Fourier Transformation) for determining the power spectrum and the leading frequency mode. This vibration frequency is converted into a biofeedback signal.

Application: measurement of muscle vibrations, determining the right compression force in garments with a negative fit; industrial applications in combination with OH&S principles.

In patients suffering from diabetic neuropathy, for example, an auditory warning signal can be implemented if the physiological COP path is not maintained or if the COP approaches an overloaded area (area with higher pressure magnitude over time, or highest pressure impulse with time, or an area affected by a sin sole ulcer.

Due to the missing feedback from the mechanoreceptors to the brain, neuropathic patients suffer from disturbed motion coordination and loss of skin sensitivity to high pressure. The width of the "sweet COP path" as well as the diameter of "hotspots" will be pre-set by a variable, the excess of which will cause the melody signal to decay and be overwritten by an alarm signal. This principle provides a training system for improvement of disturbed gait in neuropathic patients as well as minimising the risk of developing ulcers and avoiding overloading existing ulcers.

A signal magnitude is converted to a pitch signal by a non-linear function, as the frequency differential between music notes increases with the frequency and follows an exponential function.

$$f = c\, e^{p-p_0} + f_0$$

where f is the frequency of the pitch, c is a constant multiplier, $f_0$ is the minimum frequency of the pitch, p is the instantaneous pressure magnitude and $p_0$ is the pressure threshold. The non-linear function of this equation can be, for example, exponential, polynomial, etc.

If, for example, the polar angle of the COP is converted into an acoustic biofeedback signal, then the angle theta ranges from 0 deg to 360 deg. If the output frequency f should range from 100 Hz to 1000 Hz, then the corresponding equation is $$f = 10^{\frac{\theta}{360}+2}$$

or, alternatively $$f = \frac{\left(\frac{\theta}{147}+9\right)^{10}}{39000000} + 10$$

As a different solution, the pressure-sensitive area, within which the COP can move, is segmented into different sectors, either based on Cartesian COP coordinates, COPx and COPy, or on polar coordinates (□ and R), and each sector is affiliated with a specific sound (defined by the sound frequency or pitch) or a melody, such that a melody or tune can be played by moving the COP into different sectors.

The visual biofeedback signal is displayed on a screen or by means of a light source (e.g. LED). The coding parameters of a visual biofeedback signal can be:
  colour hue;
  brightness (grayscale) or intensity (lux);
  frequency of a blinking light source;
  position of a light source, or pixel on a screen.

The biofeedback signal can also be administered as a tactile signal (vibrations frequency, magnitude, or location of vibrations pressure; and with electrical stimulation).

The algorithms outlined above are embedded in the microcontroller and/or the external device (e.g. smart phone, computer).

Auditory biofeedback system is sent to earphones or speaker
a) real-time and directly from the microcontroller via RF signal (if the algorithm is embedded in the microcontroller);
b) raw data from the microcontroller via Bluetooth (zigbee, ant+, etc.) signal to smartphone or computer for further audio processing (if the algorithm is embedded in the smartphone app or computer software) and subsequent real-time output via earphones or speaker.

Visual biofeedback system is sent to a screen (smartphone, computer) as raw data from the microcontroller via Bluetooth (zigbee, ant+, etc.) signal to smartphone or computer for further processing and graphical visualisation.

Summary of Main Components of the Device
Minimum number of components:
  Material for measuring pressure (pressure sensitive material; resistive, capacitive or piezoelectric)
  Circuit for data recording
  Algorithms for calculating advanced pressure parameters from pressure raw data
  Algorithms for calculating biofeedback signals (pitch- and volume-coded auditory signal; 2D or 3D colour- and brightness coded visual signal in terms of an image or graph)
  Means for data transfer (wireless, tethered)
  Means for output (earphones, speaker, smartphone, computer, etc.) of the biofeedback signal
  Materials may be conductive polymers/elastomers in solid, cellular form (foam), and fabric form.

Advanced pressure parameters may be location and speed of centre of pressure, magnitude of pressure rate; pressure impulse; hotspot location; distribution of the COP about its average point; fractal dimension of the COP movement.

Proper biofeedback (acoustic, visual) depends on
1) accurate determination (measurement) of pressure parameters
  (e.g. location and speed of centre of pressure; magnitude of pressure rate; pressure impulse; hotspot location); and 2) algorithms for converting the raw pressure data to advanced pressure parameters and ultimately to auditory and visual signals.

Accurate determination (measurement) of pressure parameters depends on
1) sufficient sensor density and even sensor distribution, and
2) sufficient sensor resolution (size).

Both parameters affect the number of sensors required and ultimately the costs of the smart device.

The costs refer to the costs per sensor, number of sensors required for accurate measurement, and manufacturing (connection of sensors to the recording device). It is therefore desirable to use low-cost sensors, or no sensors at all by using the existing material as a sensor (sensorless sensing).

This refers to
1) a shoe insole can be made of vinyl (1 sqcm=max. 1 ct; 1 insole for max $1-$1.5) and additional placing an electrode grid (plus incorporated leads) above and beneath the insole; the vinyl material works like a sensor, therefore no further sensors are required;
2) a helmet is lined with protective and energy-absorbing foam; the foam works like a sensor (static foam), thus it suffices to place an electrode grid on the foam liner.

This invention works with any type of sensor, from expensive to cheap; the costs make the product competitive. This invention provides methods of converting raw pressure data to advanced pressure data and to converting them to auditory and visual biofeedback signals regardless of the choice of material, which replaces conventional sensors.

For obtaining advanced pressure data from raw pressure data, a high sensor density and resolution is required which affects the price of the produce when using expensive sensors.

Cheap sensors are not as accurate as expensive ones; this drawback, however, is overcome by the high sensor density and resolution which allows for improving the accuracy with mathematical methods.

From the above it can be seen that this invention provides a cost effective and advanced sensor system that provides improved biofeed back to users.

Those skilled in the art will realise that tis invention may be implemented in embodiments other than those described without departing from the core teaching of this invention.

The invention claimed is:

1. A system for assessing head injury criterion, the system including a sensor array comprising a plurality of sensors, a processor and a signal output device, wherein the processor analyzes pressure signals input from the plurality of sensors of the sensor array to calculate at least one advanced pressure parameter, the advanced pressure parameter being any one of: instantaneous location of a center of pressure (COP) on the sensor array, magnitude of the COP, speed of movement of the COP, direction of movement of the COP and distribution of the COP within a time period, and the processor calculates an impact force on an impact area of the sensor array encompassing one or more of the plurality of sensors by integrating pressure signals input from the one or more sensors in the impact area over a time within which an impact occurs, and determines a linear acceleration perpendicular to the impact area based on the calculated impact force and an effective mass of the wearer's head, and wherein the processor determines a head injury criterion (HIC) for assessment by determining a maximal HIC value from a plurality of HIC values each calculated by multiplying an integral of the linear acceleration over a time period by the inverse of the time period, raising this product to the power of 2.5, and multiplying the result by the time period; wherein the time period is a variable time window having a duration ranging between 1 millisecond and 15 milliseconds and variable starting time, whereby variable time period window acts as a sliding window continuously slid across the time within which the impact occurs combining different time periods and initial times for iterative calculation of HIC values from which only the maximal HIC value is taken, and converted to an auditory, visual or tactile biofeedback signal by the output.

2. The system as claimed in claim 1, wherein the sensors of the sensor array are evenly distributed over a measurement area.

3. The system as claimed in claim 2, wherein the processor calculates the instantaneous COP measurement using the formulae $$COPx = \sum_{i=1}^{n} \frac{x_i p_i}{n}; \quad COPy = \sum_{i=1}^{n} \frac{y_i p_i}{n}$$

where COPx and COPy are the coordinates of the COP; $x_i$ and $y_i$ are distances of an $i^{th}$ sensor from an origin of a sensor matrix coordinate system; $p_i$ is pressure on the $i^{th}$ sensor, and n is a total number of sensors.

4. The system as claimed in claim 2, wherein a magnitude for an instantaneous COP is converted to an auditory biofeedback signal, and the magnitude of the instantaneous COP is converted to a pitch signal by a non-linear function, where frequency of the pitch is a polynomial or exponential function of the instantaneous COP magnitude.

5. The system as claimed in claim 4 wherein the magnitude is converted to a pitch signal by a non-linear function, $f = c \, e^{p-p0} + f_0$ where f is a frequency of the pitch, c is a constant multiplier, $f_0$ is a minimum frequency of the pitch, p is the instantaneous COP magnitude and p0 is pressure threshold.

6. The system as claimed in claim 1, wherein a magnitude of an advanced pressure parameter is converted to an auditory biofeedback signal, and the magnitude of the advanced pressure parameter is converted to a pitch signal by a non-linear function, where a frequency of the pitch is a polynomial or exponential function of an instantaneous pressure magnitude.

7. The system as claimed in claim 1, wherein the auditory biofeedback signal is pitch- and/or volume-, and/or melody-coded.

8. The system as claimed in claim 1, wherein the visual biofeedback signal is colour- and/or brightness-coded, and/or a flashing light signal, and/or a display on a screen.

9. The system as claimed in claim 1, wherein the tactile biofeedback signal involves vibrations, pressure, or electrical stimulation.

10. The system as claimed in claim 1, wherein a position of the instantaneous COP is determined by averaging a product of pressure magnitude and x- or y- coordinate of each sensor along x- and y-axes of a Cartesian sensor matrix coordinate system, whereby the instantaneous COP is expressed in terms of x- and y-coordinates of a Cartesian coordinate system or in terms of angle and radius of a polar coordinate system.

11. The system as claimed in claim 1, wherein a velocity of the instantaneous COP is determined by the processor by differentiating displacement of the COP in x- and y-directions with time.

12. The system as claimed in claim 1, wherein a distribution of the COP about a COP average point is calculated by the processor from standard deviation, root mean square, skew, or Kurtosis of the COP in x- and y-directions, or from a size of the area containing maximally 100% of the COP-locations within a defined time period.

13. The system as claimed in claim 1, wherein a fractal dimension of the movement of the COP in x- and/or y-direction is calculated by the processor and a magnitude of the fractal dimension is converted to biofeedback signals.

14. The system as claimed in claim 1, wherein a pressure rate of at least one sensor is determined from differentiating the pressure signals from the at least one sensor with time.

15. The system as claimed in claim 1, wherein the linear acceleration perpendicular to the impact area of the sensor array is calculated by dividing the impact force by an effective mass of the object, body, or parts of the body, which the sensor array is attached to or in contact with, the linear acceleration is adjusted for a user-induced acceleration calculated from the linear acceleration by vector subtraction of gravitational acceleration; and wherein a calculated magnitude of the linear acceleration is converted to biofeedback signals.

16. The system as claimed in claim 1, wherein the processor further identifies any one or more developing high pressure areas (hotspots) from pressure impulses calculated from the pressure signals of at least one sensor, and where a magnitude of the pressure impulse and/or a distance between an identified hotspot and a physiological path of the COP calculated by the processor based on direction of movement of the COP are converted to biofeedback signals.

17. The system as claimed in claim 1, wherein impact force magnitude is subjected to thresholds and the processor converts impact force magnitude determined from the pressure signals input from one or more sensors in the impact area into magnitude data for a histogram having at least two bins, and wherein the magnitude data in each bin are used for a scoring system to count a number of repetitive movements based on different force levels.

18. The system as claimed in claim 1, wherein the processor identifies vibrations by calculating fast Fourier transform of the pressure signals input by one or more sensors to determine a power spectrum, and where mean, median or impulse of the power spectrum is converted to biofeedback signals.

19. The system as claimed in claim 1 wherein the system is integrated into a helmet, hat or protective headwear.

* * * * *